US011432835B2

(12) United States Patent
Shaffer et al.

(10) Patent No.: US 11,432,835 B2
(45) Date of Patent: Sep. 6, 2022

(54) APPARATUS AND METHODS FOR CLOT ASPIRATION

(71) Applicant: Penumbra, Inc., Alameda, CA (US)

(72) Inventors: Robyn Shaffer, Kensington, CA (US); Stephen Pons, Alameda, CA (US); Kyle West, Pleasant Hill, CA (US); Alex Rabkin, San Francisco, CA (US); Sharice Quan Handa, San Ramon, CA (US); Robert A. Riccomini, Saratoga, CA (US); Daniel K. Harden, Palo Alto, CA (US); Michael C. Makay, Santa Clara, CA (US); Cole J. Derby, East Palo Alto, CA (US)

(73) Assignee: PENUMBRA, INC., Alameda, CA (US)

( * ) Notice: Subject to any disclaimer, the term of this patent is extended or adjusted under 35 U.S.C. 154(b) by 408 days.

(21) Appl. No.: 16/000,762

(22) Filed: Jun. 5, 2018

(65) Prior Publication Data
US 2018/0353194 A1    Dec. 13, 2018

Related U.S. Application Data

(60) Provisional application No. 62/516,582, filed on Jun. 7, 2017.

(51) Int. Cl.
*A61B 17/221* (2006.01)
*A61B 17/3203* (2006.01)
(Continued)

(52) U.S. Cl.
CPC ............ *A61B 17/221* (2013.01); *A61B 17/22* (2013.01); *A61B 17/3207* (2013.01);
(Continued)

(58) Field of Classification Search
CPC .......... A61M 1/0027; A61M 2205/587; A61B 2217/005; A61B 17/22; A61B 2017/22079
See application file for complete search history.

(56) References Cited

U.S. PATENT DOCUMENTS 6,027,490 A * 2/2000 Radford .............. A61M 1/0001
220/770
6,200,276 B1 * 3/2001 Biesel .................. A61M 1/0001
600/573
(Continued)

FOREIGN PATENT DOCUMENTS

WO    WO-9421312 A2 *   9/1994   .......... A61M 1/0003
WO    WO-2010089368 A2 *   8/2010   .......... A61M 1/0001

OTHER PUBLICATIONS

Science of Aspiration: The penumbra system approach. Penumbra, 2016. 4 Pages. www.penumbrainc.com.

*Primary Examiner* — Catharine L Anderson
*Assistant Examiner* — Arjuna P Chatrathi
(74) *Attorney, Agent, or Firm* — Haley Guiliano LLP (57) ABSTRACT

A system for connection to a catheter to aspirate clot from the vasculature of a patient includes a vacuum console and a canister assembly which can be removably mounted in a mounting region of the vacuum console. The canister assembly includes a clear canister with an interior and an open top. A lid is removably attachable over the open top of the clear canister, and the clear canister has a vacuum port and a pressure sensing port each formed in a wall of the canister. The vacuum port aligns with a vacuum connector on the enclosure and the pressure sensing port aligns with a pressure sensing connector on the enclosure when the canister assembly is mounted on the mounting region of the vacuum console. The clear canister has a filter plate configured to be suspended in the interior of the clear canister at a location mid-way between the open top and a bottom to separate clot from blood as they are aspirated from the catheter.

12 Claims, 7 Drawing Sheets

(51) Int. Cl.
*A61B 17/3207* (2006.01)
*A61M 1/00* (2006.01)
*A61B 17/22* (2006.01)

(52) U.S. Cl.
CPC ..... *A61B 17/32037* (2013.01); *A61M 1/0001* (2013.01); *A61M 1/732* (2021.05); *A61M 1/79* (2021.05); *A61B 2017/22079* (2013.01); *A61B 2017/22084* (2013.01); *A61B 2217/005* (2013.01); *A61M 1/80* (2021.05); *A61M 2205/587* (2013.01)

(56) References Cited

U.S. PATENT DOCUMENTS

| | | | | |
|---|---|---|---|---|
| 6,280,429 B1 * | 8/2001 | Lewis | ..................... | A61M 1/79 604/4.01 |
| 7,497,340 B2 * | 3/2009 | Hershberger | .......... | B01D 29/03 210/136 |
| 7,955,318 B1 * | 6/2011 | Schultz | ................... | A61M 1/84 604/319 |
| 8,366,694 B1 * | 2/2013 | Jordan | ..................... | A61M 1/79 604/319 |
| 9,095,326 B2 * | 8/2015 | Ritchie | ............... | A61B 10/0266 |
| 9,322,748 B1 * | 4/2016 | Kimsey, II | .......... | A61M 1/0023 |
| 2003/0042187 A1 * | 3/2003 | Menne | ................ | B01D 29/018 210/136 |
| 2004/0024360 A1 * | 2/2004 | Greter | ..................... | A61M 1/80 604/133 |
| 2004/0160770 A1 * | 8/2004 | Rodriguez | .......... | A61M 5/1417 362/234 |
| 2005/0197640 A1 * | 9/2005 | Say | ..................... | A61M 1/0023 604/319 |
| 2005/0209585 A1 * | 9/2005 | Nord | ........................ | G01F 3/38 604/540 |
| 2007/0191731 A1 * | 8/2007 | Kaye | .................. | A61B 10/0283 600/565 |
| 2011/0068061 A1 * | 3/2011 | Eagle | .................. | A61M 1/3627 210/780 |
| 2015/0359949 A1 * | 12/2015 | Yeager | ..................... | A61M 1/79 435/283.1 |

* cited by examiner

APPARATUS AND METHODS FOR CLOT ASPIRATION

CROSS-REFERENCE TO RELATED APPLICATION

The present application claims the benefit of provisional application No. 62/516,582 (Attorney Docket No. 41507-725.101), filed on Jun. 7, 2017, the full disclosure of which is incorporated herein by reference.

BACKGROUND OF THE INVENTION

1. Field of the Invention

The present invention relates generally to the field of medical devices and methods. More specifically, the invention described herein relates to devices and methods for aspirating clot removed from a patient's vasculature by thrombectomy.

Stroke is a significant cause of disability and death, and a growing problem for global healthcare. More than 700,000 people in the United States alone suffer a stroke each year, and of these, more than 150,000 people die. Of those who survive a stroke, roughly 90% will suffer long term impairment of movement, sensation, memory, or reasoning, ranging from mild to severe. The total cost to the U.S. healthcare system is estimated to be over $50 billion per year.

Stroke may be caused by a blockage in a cerebral artery resulting from a thromboembolism (referred to as an "ischemic stroke"), or by a rupture of a cerebral artery (referred to as a "hemorrhagic stroke"). Hemorrhagic stroke results in bleeding within the skull, limiting blood supply to brain cells, and placing harmful pressure on delicate brain tissue. Blood loss, swelling, herniation of brain tissue, and pooling of blood that results in formation of clot mass inside the skull all rapidly destroy brain tissue. Hemorrhagic stroke is a life-threatening medical emergency with limited treatment options.

Aside from cerebral stroke, thromboembolism throughout the vasculature, in both arterial and venous circulation, is characteristic of numerous common, life-threatening conditions. Examples of potentially fatal diseases resulting from thrombotic occlusion include pulmonary embolism, deep vein thrombosis, and acute limb ischemia. Acute pulmonary embolism is a significant cause of death in the United States, with roughly 300,000 patients dying each year. Pulmonary embolism can be a complication from deep vein thrombosis, which has an annual incidence of 1% in patients 60 years and older. All of the aforementioned diseases are examples of conditions in which treatment may include aspiration or evacuation of clot and/or blood.

Figure 1:
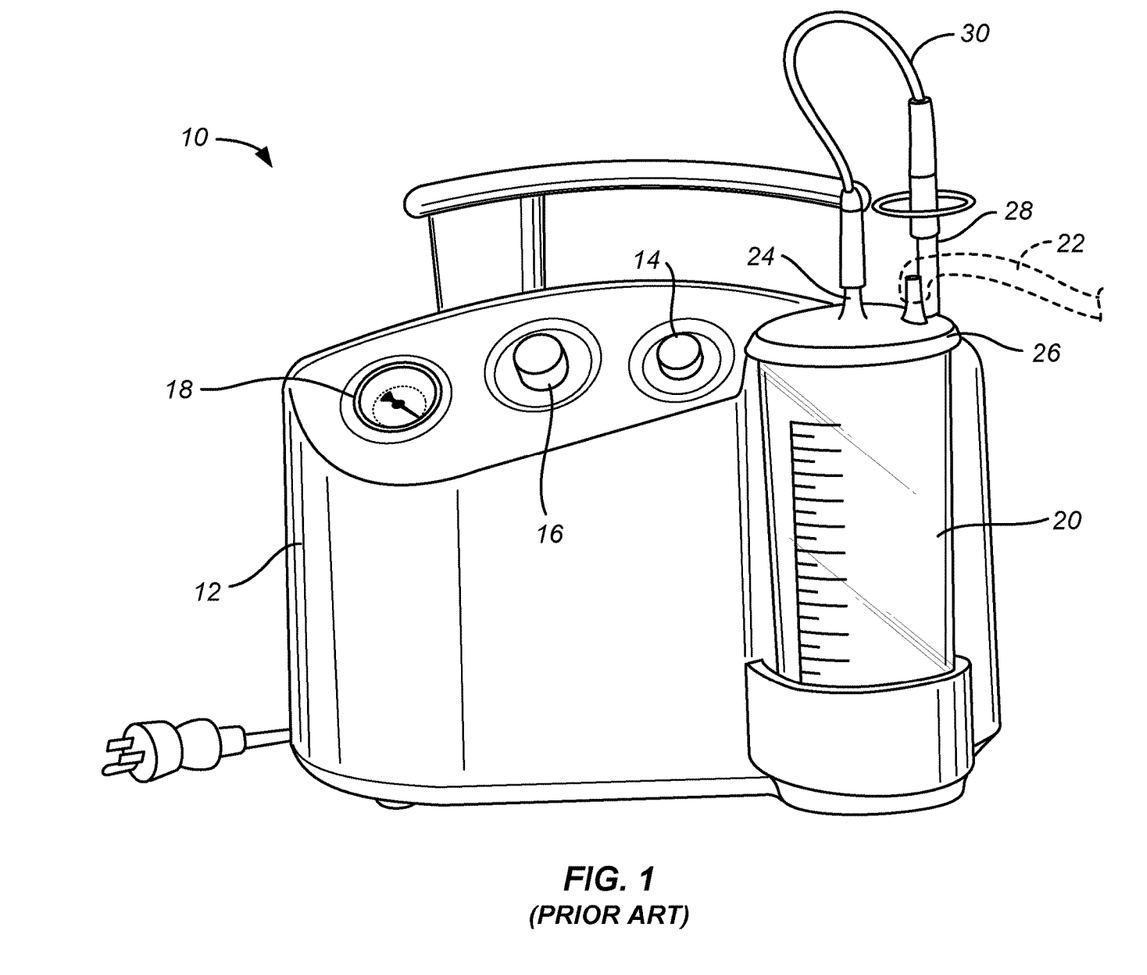
FIG. 1 illustrates the vacuum console and collection canister of the Penumbra System® mechanical thrombectomy system as described in detail in the Background of the Invention above.

Of particular interest to the present invention, the Penumbra System® mechanical thrombectomy system is a fully-integrated system designed specifically for mechanical thrombectomy by aspiration. It is intended for revascularization of patients with acute ischemic stroke secondary to intracranial large vessel occlusion. The Penumbra System is commercially available at the time of filing the present provisional patent application and includes reperfusion catheters, aspiration tubing, and an aspiration pump console (sold under the tradename: Pump MAX™ aspiration pump) for connection to the aspiration tubing and reperfusion catheters. As illustrated in FIG. 1, the Pump MAX™ aspiration pump 10 includes a base unit 12 which encloses a vacuum pump (not shown) which operates off line current. The base unit has an on-off switch 14 and a separate knob 16 for adjusting the level of vacuum provided by the pump. The vacuum level can be read on a pressure gauge 18. Blood and clot are drawn into a collection canister 20 from an aspiration tube 22 (shown in broken line) which is connected to a reperfusion catheter (not illustrated) which has been introduced to the cerebral vasculature of a patient to aspirate clot. The blood and clot are drawn into the collection canister by a partial vacuum which is provided by a vacuum connector 28 on the base unit 12 which is connected to the vacuum pump, not shown. The vacuum from vacuum connector 28 is applied to a vacuum port 24 on a removable lid 26. The vacuum connector 28 is connected to the vacuum port 24 by an external vacuum tube 30.

Although very effective, the use of the Pump MAX™ aspiration pump as part of the Penumbra System® has certain shortcomings. First, the external vacuum tube 30 required by the presently available Pump MAX™ aspiration pump can become entangled with the aspiration tube 22 and is also subject to accidental disconnection during a procedure. Second, the pressure measurement shown on gauge 18 is measured in an internal line connected to the vacuum connector 28, and can be affected by ambient pressure which can differ based on elevation above sea level. Should that line become clogged, the pressure reading which is supposed to represent the pressure within the canister will be inaccurate. Third, the canister 20 is clear to allow the physician to view the nature and amount of clot being removed. It can be difficult, however, to visually distinguish the clot from the blood that is also being removed, particularly in a darkened cath lab.

In order to evaluate clot material removed, the clinician is often required to remove canister 20 from its connection to base unit 12, so that the extracted contents can be poured out, and any clot material poured onto gauze or similar material, for viewing. The foregoing steps can be messy, inconvenient, and require careful manipulation to avoid increased risk of aseptic contact with blood.

Therefore, it would be desirable to provide improved pumping consoles and apparatus and methods for clot extraction, and at least some of these objectives discussed above will be met by the inventions described herein below. These systems should be suitable for use with clot extraction systems intended for use with patients suffering pulmonary embolism, deep vein thrombosis, peripheral artery disease, and other conditions as well as stroke.

2. Description of the Background Art

The Penumbra System® as it was commercially available at the time of filing provisional patent application No. 62/516,582 is described in a brochure entitled "Science of Aspiration: The Penumbra System® Approach."

SUMMARY OF THE INVENTION

The present invention provides improved vacuum systems including a vacuum console and a collection canister for use with mechanical thrombectomy systems, such as with reperfusion catheters of the type which are used in the Penumbra System®, the Indigo® Aspiration System mechanical thrombectomy system, and other systems used for the therapeutic extraction of clot and/or blood and other fluids. Use of the vacuum console and collection canister of the present invention, however, is not limited to any particular thrombectomy system, and the vacuum systems can find use with any thrombectomy, embolectomy, atherectomy, or other catheter or probe system where blood and clot are withdrawn wholly or partially by application of a vacuum to the proximal end of any reperfusion catheter, aspiration catheter or probe for the purpose of clot extraction.

The vacuum consoles and collection canisters of the present invention provide a number of advantages over previous vacuum systems. For example, the vacuum console of the present invention provides a direct connection between a vacuum pump within the console and an interior of a removable canister which collects the clot and blood from the associated catheter. Such a design simplifies connection and routing of the catheter to the vacuum console. In particular, since there is no external vacuum tube, entanglement of the aspiration tube with external vacuum tubes on the vacuum console is eliminated. Additionally, the vacuum consoles and associated clot collection canisters of the present invention provide for improved pressure sensing within the interior of the canister. By providing a pressure sensor which measures vacuum pressure directly in the collection canister, the risk of clogging of the pressure pathway is greatly reduced. Still further, the vacuum console of the present invention provides improved visibility of clot which is being collected within the collection canister. Additional features of the improved design include improved lighting and a quick connect fitting for attachment of the catheter.

In a first aspect, the present invention provides a clot collection or other canister assembly for removably mounting on or in a mounting region on a vacuum console which has a vacuum connector configured to be connected to a vacuum pump and a pressure sensing connector configured to be connected to a pressure sensor. The canister comprises a clear canister body with an interior and an open top. A lid is removably attachable over the open top of the clear canister, and the clear canister has a vacuum port and a pressure sensing port each formed in a wall of the canister. The vacuum port on the clear canister aligns with the vacuum connector on the vacuum console when the canister assembly is mounted on or in the mounting region of the vacuum console. Similarly, the pressure sensing port on the clear canister aligns with a pressure sensing connector on the vacuum console when the canister assembly is mounted on the mounting region of the vacuum console. In this way, reliable connections are formed between the connectors on the vacuum console and the ports on the clear canister simply by mounting the canister on the vacuum console. The absence of external tubing connecting the vacuum console to the vacuum canister reduces clutter and the risk of entanglement with the catheter or other intermediate tubing, such as aspiration tubes. The absence of external tubing also saves time by eliminating the need to make two connections both during both installation and removal of the canister. Additionally, the separate connections provided for drawing a vacuum within the clear canister and for sensing pressure within the clear canister allow the pressure sensor to operate reliably even when the vacuum pathway may be partially or totally clogged with clot or other debris.

In specific embodiments, an aspiration port for connection to the catheter or other intermediate tubing is provided on the removable lid. The aspiration port may take a variety of forms. For example, the port may be a simple tubular, typically male, connector for coupling directly or indirectly to the catheter, e.g. through an aspiration tube. Additionally or alternatively, the aspiration port may include a threaded connector for mating to a threaded connector on the proximal end of the catheter or aspiration tube. In further embodiments, the aspiration port may include both a tubular connection portion and a threaded connector portion allowing connection to corresponding connectors on the catheter or aspiration tube. Still more particularly, threaded connectors of the present invention may also have mating detents on the connector in order to interface with detents on the proximal end of a catheter or other intermediate tubing, so that a user may tactilely sense when the connection is complete.

In other specific embodiments of the canister assembly, a filter plate may be suspended in the interior of the clear canister at any location. In specific embodiments, the filter plate may be positioned in the upper half of the canister so that it will not become submerged in blood. In the illustrated embodiment, the filter plate is located mid-way between the open top and a bottom of the canister. By "mid-way" this meant that the filter plate will usually be in the middle one-third of the clear canister between the top and bottom. The filter plate will typically be perforated or formed as a woven or other screen or similar barrier which allows the liquid blood to flow through the plate while retaining all or substantial portions of the clot entrained in the blood on an upper surface of the plate. The filter plate will usually extend across substantially an entire cross-section of the interior of the canister, but will often leave an open portion for blood overflow should the oncoming blood flow rate exceed the flow through the filter plate itself. In specific examples, the filter plate will be inclined at an angle relative to horizontal so that one edge of the plate is lower than the other. An open space left will typically be left between an upper end of the plate and the interior wall of the canister so that clot will flow downwardly and collect at the lower edge and blood may overflow at the upper edge, reducing the risk that the clot will overflow in the open space left within the canister. In such designs, the lower edge of the plate will typically seal against the interior wall of the canister, reducing the risk of clot flowing past that edge and diverting blood flow to the open region at the upper end of the plate. The lower edge typically also has an upwardly extending lip that helps contain the clot on the upper surface of the filter plate.

In still further specific embodiments of the canister assembly, the vacuum port and the pressure sensing port are each formed in the wall at a location mid-way between the open top and a bottom of the vacuum canister. In particular, the vacuum port and the pressure sensing port will each comprise riser tubes which are open at their upper ends so that the vacuum is drawn and the pressure is sensed near the top of the canister. This design is advantageous since it further reduces the risk that clot or blood entering the canister will flow into either the vacuum port or the pressure sensing port and interfere with operation of the vacuum console and also increases the usable volume of the canister. Optionally, at least the vacuum port will have a filter element in a lumen thereof, typically a lumen within the riser, in order to still further reduce the risk of blood or clot entering the vacuum pump and vacuum console.

In a second aspect, the present invention provides a canister assembly for removable mounting on a mounting region of the vacuum console which has a vacuum connector connected to a vacuum pump and a pressure sensing connector connected to a pressure sensor. The canister assembly comprises a clear canister with an interior and an open top. A lid is removably attachable over the open top of the clear canister, and the clear canister has filter plate configured to be suspended in the interior of the clear canister typically at a location mid-way between the open top and a bottom.

Details of the construction and design of the filter plate are described above in connection with the first aspect of the present invention. The canister assembly having the filter plate may further optionally comprise a vacuum port and a pressure sensing port each formed in a wall of the canister. The design of these vacuum ports in connection with the vacuum connectors on the vacuum console, are also fully described above in connection with the first aspect of the present invention.

In a third aspect, the present invention provides a vacuum console for removably receiving a canister assembly including a clear canister with an interior and open top and a lid removably attachable over the open top of the clear canister. The vacuum console comprises an enclosure having a mounting region for removably receiving the canister assembly. A vacuum pump and a pressure sensor are disposed within the enclosure, and a vacuum connector is connected to the vacuum pump and a pressure sensing connector is connected to the pressure sensor, where both connectors are located on the enclosure at a location in or adjacent to the mounting region. When the canister assembly is received within the mounting region of the vacuum console, the vacuum connector will align with a vacuum port formed in a wall of the canister and the pressure sensing connector will align with a pressure sensing port formed in a wall of the canister.

In specific embodiments of the vacuum console, the vacuum connector and the pressure sensing connector are located within the mounting region of the enclosure so that the connectors are covered by the clear canister assembly when the canister is received in the mounting region of the vacuum region of the vacuum console. At least one light is preferably provided within the mounting region, where the light is oriented to direct light across the clear canister when the canister is received in the mounting region. The illustrated embodiment includes two lights, one on a right side of the canister and one on a left side of the canister and both oriented to direct light inwardly to illuminate the interior of the canister. Such light will illuminate the contents of the clear canister which is of particular advantage when procedures are performed in a darkened fluoroscopy suite. The vacuum console may further comprise a light bar display on the top of the enclosure, where the light bar display indicates a percentage of pressure detected by the pressure sensor in the canister assembly. Typically, the light bar display will be circular and segmented into quadrants.

Additionally, the vacuum systems of the present invention will typically provide the ability to measure vacuum as a percentage ambient pressure. A first sensor measures ambient pressure external to the enclosure and a second sensor measures the reduced pressure inside the canister. By having both pressures, the system can calculate and display "vacuum in the canister" as a percentage of ambient pressure. This normalized value is not affected by ambient pressure, which can differ based on elevation above sea level.

In further aspects of the present invention, systems may be provided including both vacuum consoles as described above in combination with canister assemblies as described above. The systems may have any of the permutations and combinations of features as described previously.

DETAILED DESCRIPTION OF THE INVENTION

Some embodiments of the inventions of the present application are described below. For clarity, not all features of each actual implementation are described in this specification. In the development of an actual device, some modifications may be made that result in an embodiment that still falls within the scope of the invention.

Figure 2:
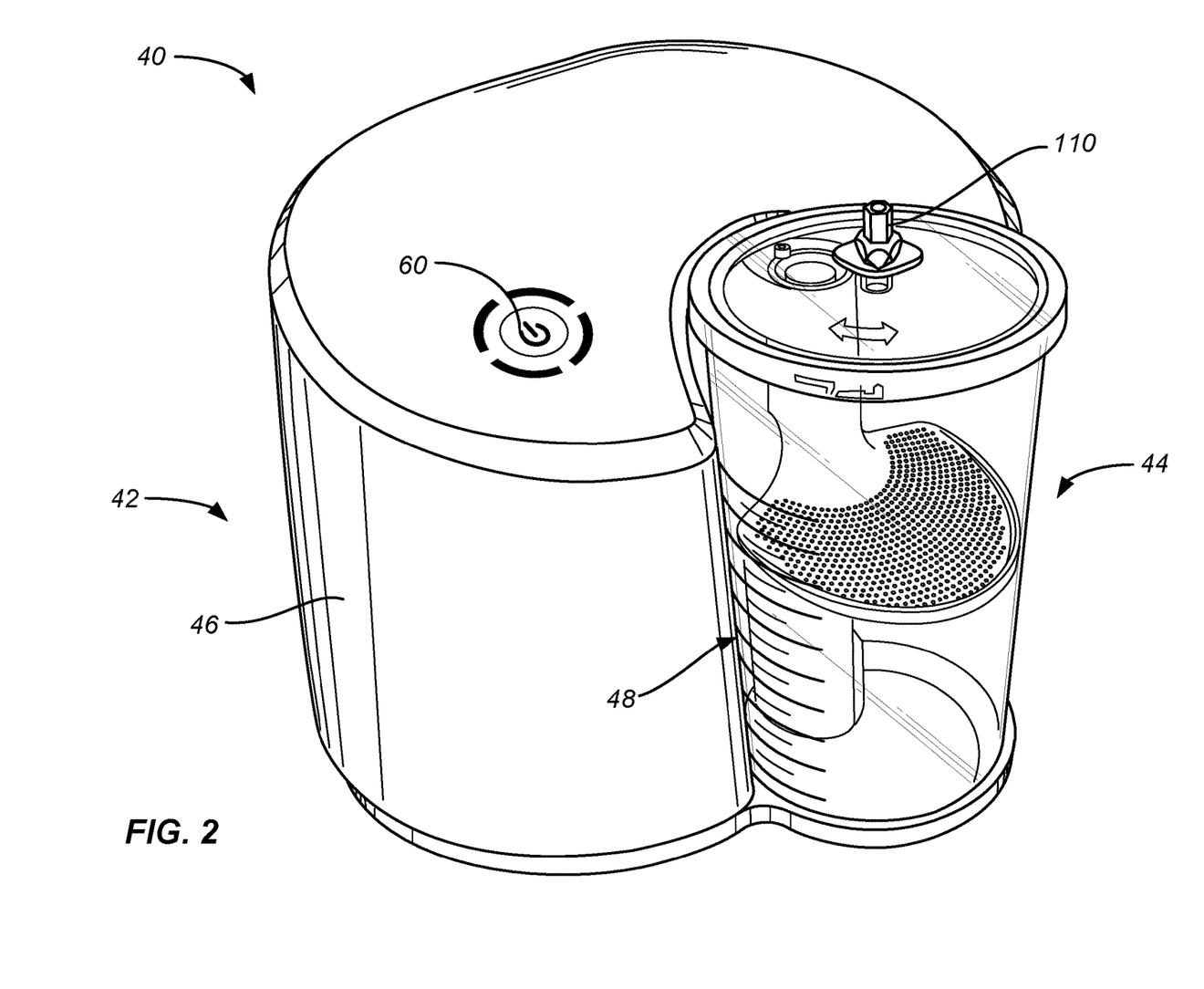
FIG. 2 is a perspective view of a vacuum console and a blood and clot collection canister constructed in accordance with the principals of the present invention with the collection canister received in a mounting region of the vacuum console.

Referring to FIG. 2, a vacuum system 40 constructed in accordance with the principles of the present invention includes a vacuum console 42 and a blood/clot collection canister 44. The vacuum console 42 comprises of an enclosure having a recess 48 which is shaped to removably receive the collection canister 44 as will be described in more detail below.

Figure 3A:
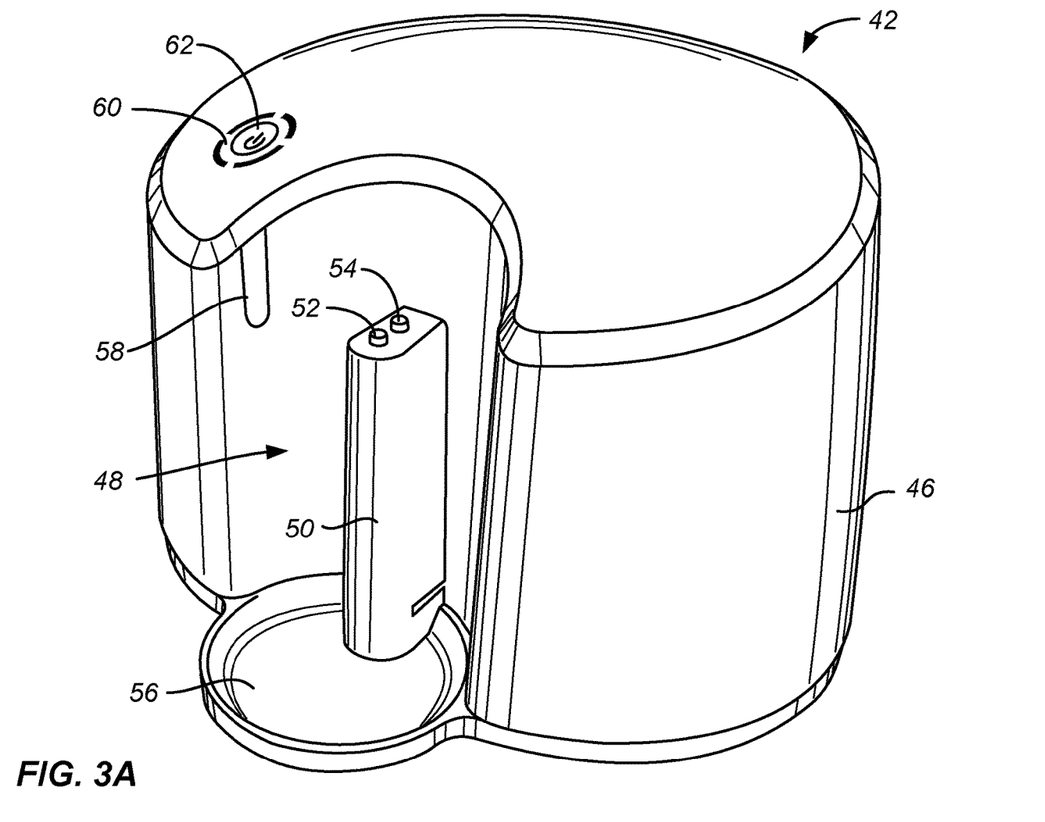
FIG. 3A is a view of the vacuum console of the present invention shown with the collection canister removed.
Figure 3B:
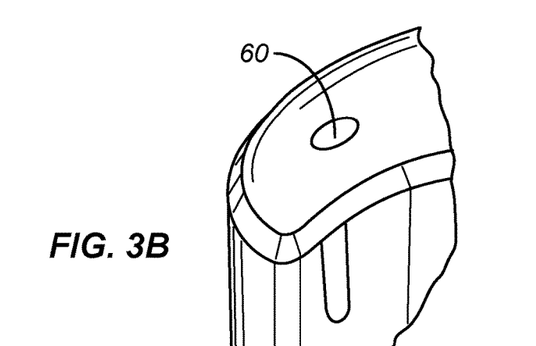
FIG. 3B is a detailed view of the on-off switch and a vacuum display region on a top surface of the vacuum console of FIG. 3, shown with the power off.
Figure 3C:
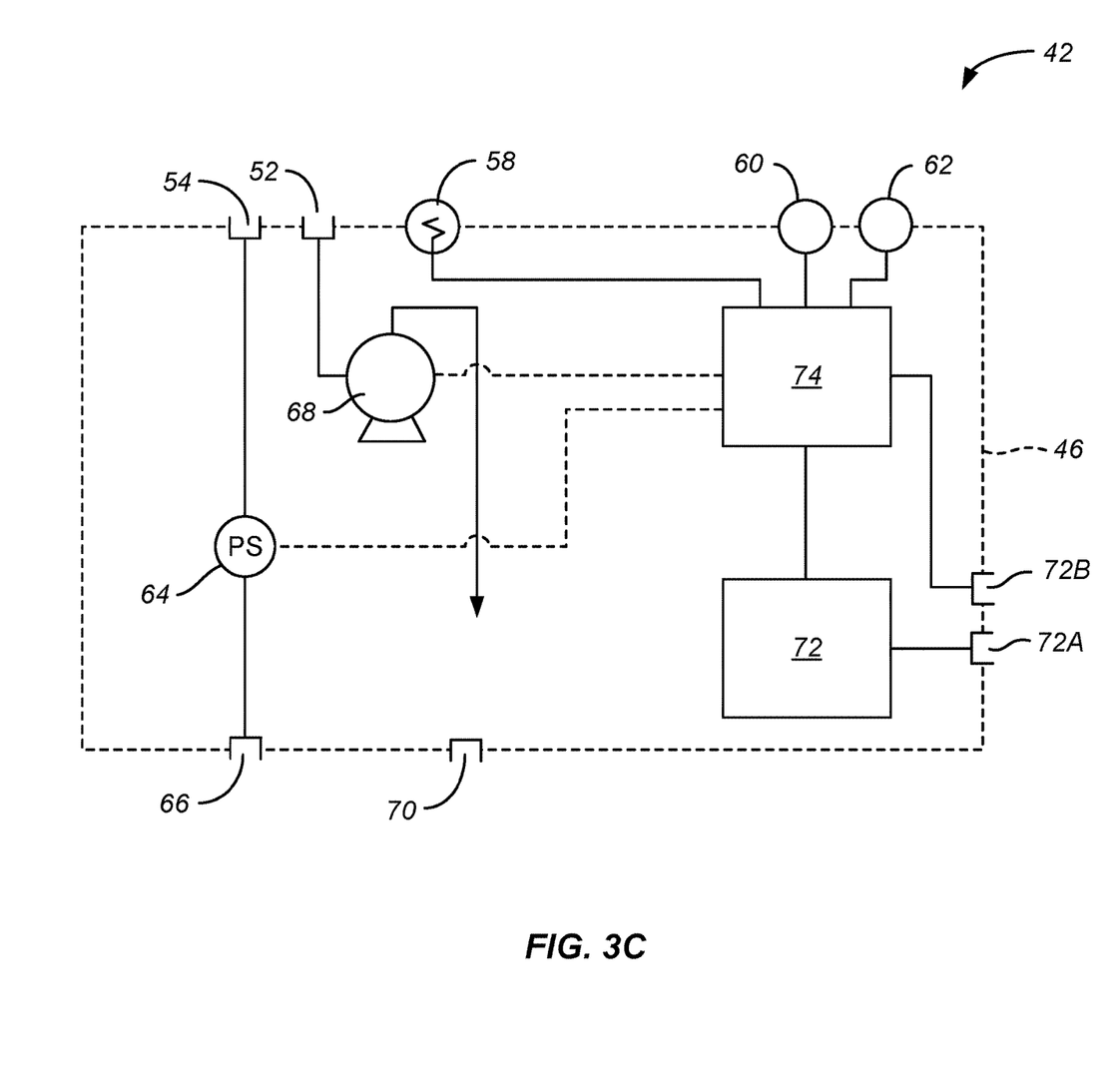
FIG. 3C is a schematic representation of the internal components of the vacuum console of FIGS. 1 to 3A.

Referring to FIGS. 3A-3C, the vacuum console 42 is shown with the vacuum canister 44 removed. A post 50 which forms a contiguous portion of the outer surface or wall of the enclosure 46 is formed within the recess 48 and extends upwardly from a bottom plate 56 which acts as a support for the collection canister 44 when it is received within the recess. A vacuum connector 52 and a pressure sensing connector 54 are formed in or on an upper surface of the post 50 and are located so that they will align with a pressure sensing port 104 and a vacuum port 102 (FIG. 5) on the vacuum canister 44 when it is received within the recess 48. One light 58 is located on a wall surface of the enclosure 44 within the recess 48 and is located so that it will illuminate the contents of the collection canister 44 when the system is in use. A second light (not visible in in FIG. 3A) is present on the opposite wall of the recess 48. The vacuum console 42 also has an on-off switch 60 on its upper surface. The on-off switch 60 illuminates when it is on (as shown in FIGS. 2 and 3A) and is not illuminated when the system is off (FIG. 3B). Additionally, a pressure display 62 is provided on the upper surface of the enclosure 46. As shown in FIGS. 2 and 3A, the display may be a circular light, e.g. having four segments which are sequentially illuminated as the vacuum level within the canister increases. Each quadrant represents the measured vacuum as a percentage of ambient pressure.

The internal components of the vacuum console 42 are schematically illustrated in FIG. 3C. The primary internal components of the vacuum console include a pressure sensor 64, a pump 68, a power supply 72, and a microprocessor controller 74. The pump 68 has an inlet connected to the vacuum connector 52 on the post 50 of the enclosure 46. Similarly, the pressure sensor 64 is connected to the pressure sensing connector 54 on the post 50 (FIG. 3A), where the pressure sensor is open to an external vent 66, typically on the bottom of the console. The pump can be turned on by the switch 60 and will draw vacuum through the connector 52 and release the removed gas into an interior of the vacuum console 42. The console in turn is vented by a vent 70 on a bottom surface of the enclosure 46.

The functions of the pump will be controlled by the microprocessor controller 74, and the pressure output from sensor 64 will also go through the microprocessor controller 74. Each of the light 58, switch 60, and display 62 will be connected to the microprocessor controller 74 which is powered by the power supply 72. The power supply 72 is powered through line current connector 72A. The USB connector 72B is powered by microprocessor controller 74. The pump is plugged into an outlet via a power cord that is supplied with the pump. The power supply converts the AC current from the wall outlet to 24V DC which is what the microprocessor controller uses to power the pump, switch, lights, USB connector, etc.

In specific examples, pressure sensor 64 is connected to the microprocessor controller 74 and measures vacuum pressure in the canister through the pressure sensing connector 54. A second pressure sensor (not shown) is also connected to the microprocessor controller 74 and measures ambient pressure outside of the pump enclosure through an internal tube that is routed to a vent in the base of the pump. The microprocessor controller takes the vacuum pressure reading from the pressure sensor 64 and divides it by the ambient pressure reading from the second pressure sensor to calculate the vacuum pressure in the canister as a percent of ambient pressure.

Figure 4:
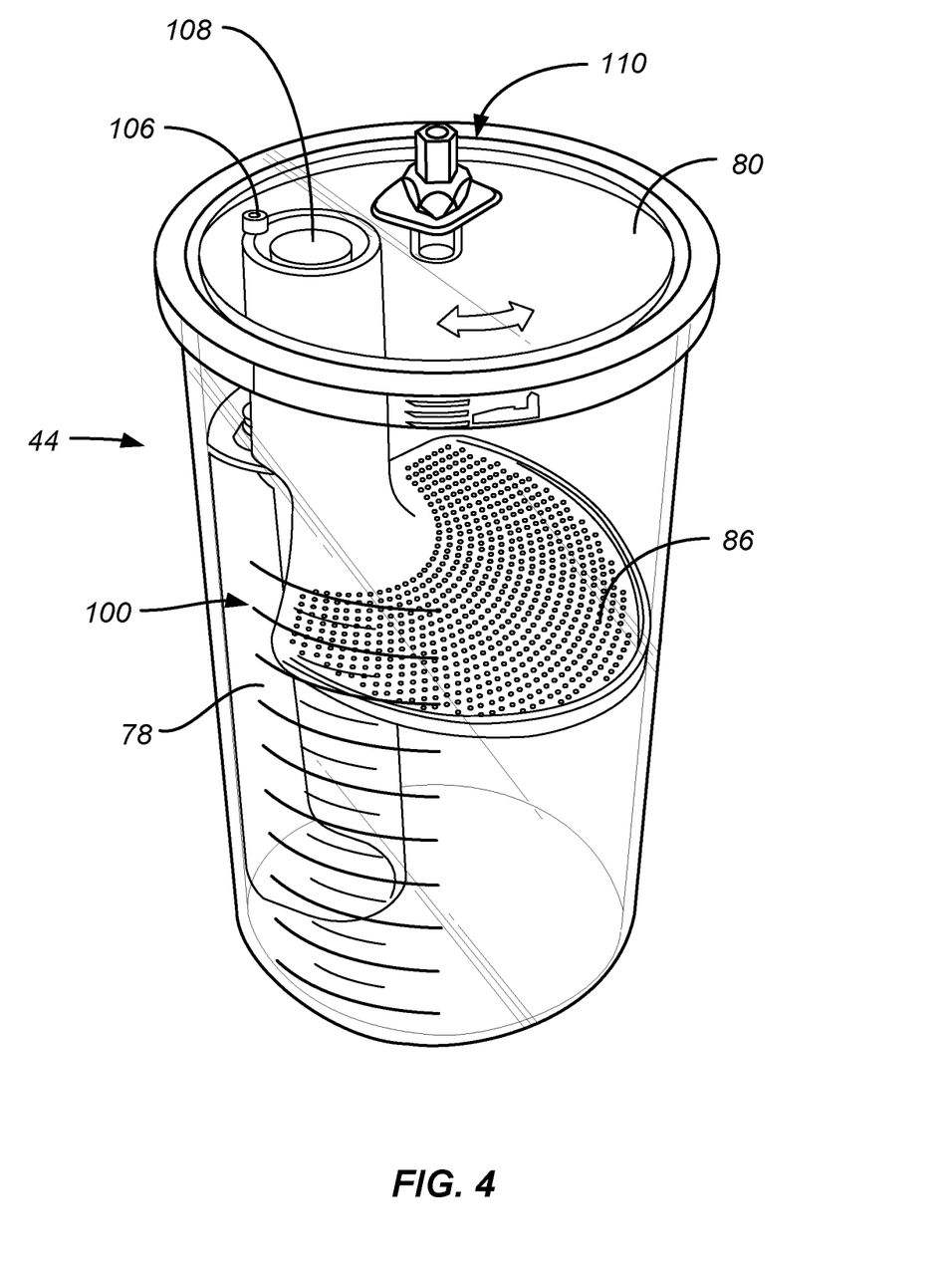
FIG. 4 illustrates a collection canister constructed in accordance with the principles of the present invention.
Figure 5:
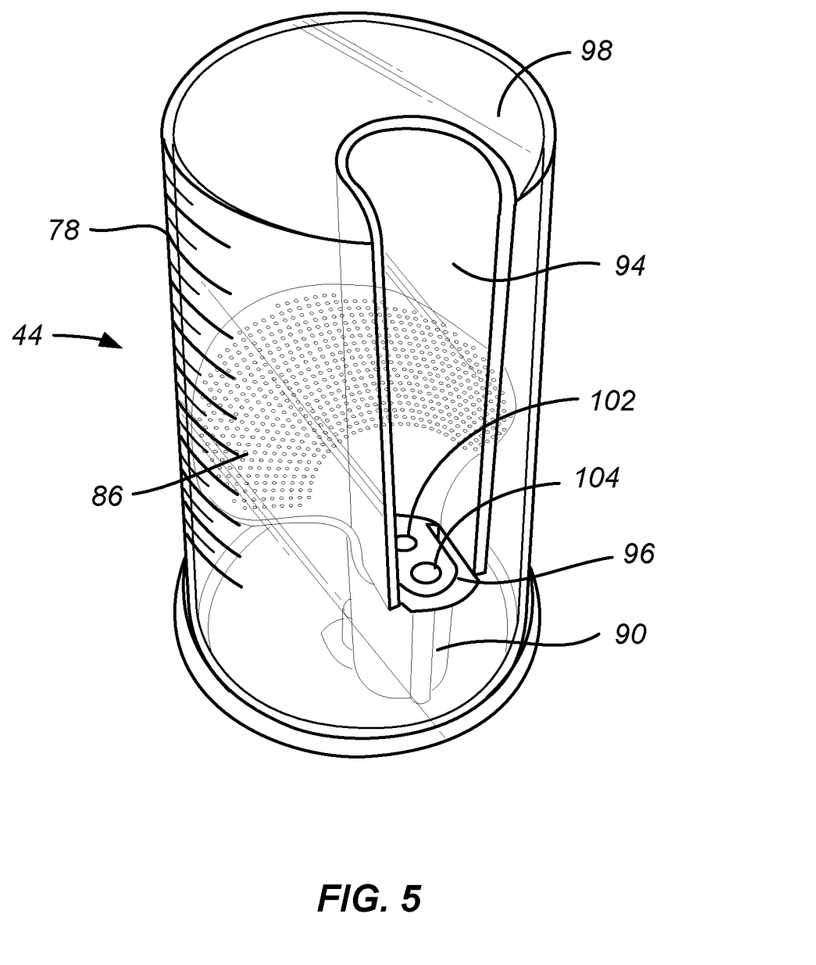
FIG. 5 illustrates the embodiment of the collection canister of FIG. 4, shown in an inverted or "upside down" view.
Figure 6:
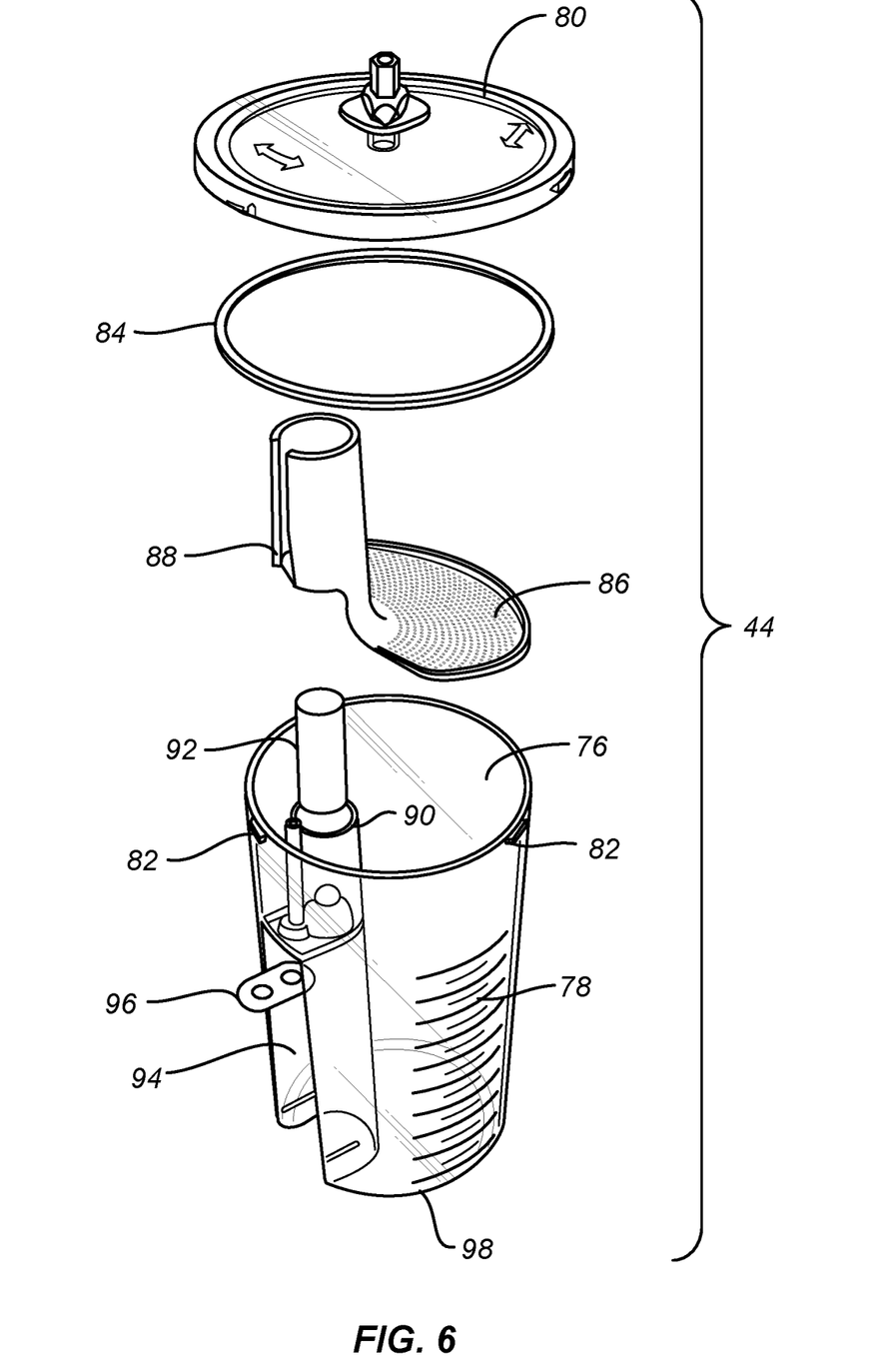
FIG. 6 is an exploded view of the vacuum canister of FIGS. 4 and 5.

Referring now to FIGS. 4-6, the collection canister 44 has a main body 78 which is typically formed from a polished, clear plastic material which is molded into the illustrated shape. The main body 78 has a base 98 with an open upper end 76 which can be covered by a removable clear plastic lid 80. The clear plastic lid 80 is typically attached by a bayonet connector 82, and a form or other gasket 84 will seal the lid to the open end of the main body 78.

A groove 94 is formed in one side of the main body 78 and is shaped so that it can be placed over the post 50 in the recess 48 of the enclosure 46 of the vacuum console 42. As best seen in FIG. 5, the pressure sensing port 104 and the vacuum port 102 are located at the upper end of the groove 94 so that they align and connect with the vacuum connector 52 and pressure sensing connector 54 on the post 50 when the canister 44 is in place in the recess 48.

The pressure sensing port 104 is connected to a tube or lumen which extends upwardly in the main body 48 of the canister 44 and terminates in an upper opening or aperture 106. Similarly, the vacuum port 102 extends upwardly through a much larger lumen or tube and terminates in an open aperture 108 at its upper end. The apertures 106 and 108 are located near the top of the interior of the main body 78 but will be below the bottom of the lid 80 when the lid is in place on the canister 44. Thus, both of the apertures 106 and 108 will be exposed to the interior of the canister 44 but will be maintained well above the mid-section and bottom where the clot and blood are collecting. In this way, the risk of contamination from blood and clot is minimized.

A filter plate 86, shown as a perforated screen but which could also be a woven screen or other separating member, is held in the mid-section of the interior of the main body 78 of the canister 44. The clot is drawn into the interior of the canister through a connector 110 which is attached to a proximal end of the catheter or other tubing. The clot and blood are drawn into the interior of the main body 78 by the vacuum which is drawn through the vacuum port 102 by the vacuum console 42, as previously described. As the clot and blood fall downwardly from connector 110 into the canister 44, the clot collects on the upper surface of the filter plate 86 while the blood flows through the perforations in the plate and collects in the bottom of the canister. As the plate is inclined downwardly from a sleeve 88 which is mounted on a post 90 in the interior of the canister, excess blood may flow over an open bypass region 100 (FIG. 4) which is formed on a backside of the plate and allows the blood to flow directly down to the bottom of the canister. Filter body 92 (FIG. 6) occupies the interior of post 90 and aperture 108, and prevents extracted material from contaminating the interior of enclosure 42. The filter body 92 can thus prevent extracted material from contaminating the interior of enclosure 42. A groove 94 is formed on a side of the main body 78 of the canister 44 and is received over the post 50 in the recess 48 of the enclosure 46 in order to align the vacuum and pressure sensing connectors and vacuum ports. A gasket 96 is further provided at the seal between the vacuum ports and the vacuum connectors.

The foregoing examples are not intended to limit the scope of the invention. All modifications, equivalents and alternatives are within the scope of the invention.

What is claimed is:

1. A canister assembly for removably mounting on a mounting region of a vacuum console which has a vacuum connector connected to a vacuum pump and a pressure sensing connector connected to a pressure sensor, said canister assembly comprising:
   a clear canister with an interior and an open top; and
   a lid removably attachable over the open top of the clear canister;
   said clear canister having a vacuum port and a pressure sensing port each formed in a groove formed in a wall of the canister, wherein the vacuum port aligns with the vacuum connector and the pressure sensing port aligns with the pressure sensing connector and the groove aligns with a mounting post of the vacuum console when the canister assembly is mounted on the mounting region of the vacuum console.

2. A canister assembly as in claim 1, wherein the lid has an aspiration port configured to removably connect to a catheter or aspiration tube.

3. A canister assembly as in claim 1, further comprising a filter plate configured to be suspended in the interior of the clear canister at a location mid-way between the open top and a bottom, wherein the filter plate includes an edge and at least a portion of the edge contacts a wall of the clear canister.

4. A canister assembly as in claim 1, wherein the vacuum port and the pressure sensing port are each formed in the wall at a location mid-way between the open top and a bottom and are each connected to riser tubes within the interior of the clear canister, wherein the riser tubes are open at their upper ends so that the vacuum is drawn and the pressure sensed near the top of the canister.

5. A canister assembly as in claim 4, wherein the riser tube connected to the vacuum port has a filter in a lumen thereof.

6. A canister assembly as in claim 2, wherein the aspiration port includes both a threaded connector and a tubular connector so that it can connect to a catheter or aspiration tube having a threaded connector or to a catheter or aspiration tube having a tubular connector.

7. A canister assembly as in claim 6, wherein the threaded connector of the aspiration port has detents configured to mate with detents on a threaded connector of the catheter or aspiration tube.

8. A vacuum console for removably receiving a canister assembly, said vacuum console comprising:
- an enclosure having a mounting post, formed within a recess in the enclosure, that aligns the canister assembly during mounting;
- a vacuum pump and a pressure sensor within the enclosure; and
- a vacuum connector connected to the vacuum pump and a pressure sensing connector connected to the pressure sensor;
- wherein the vacuum connector aligns with a vacuum port of the canister assembly and the pressure sensing connector aligns with a pressure sensing port of the canister assembly when the canister assembly is mounted.

9. A vacuum console as in claim 8, wherein the vacuum connector and the pressure sensing connector are located on a top surface of the mounting post.

10. A vacuum console as in claim 9, wherein the vacuum connector and the pressure sensing connector are abutting on the top surface of the mounting post.

11. A vacuum console as in claim 8, wherein the mounting post is vertical and extends from a bottom of the enclosure to at least a midway height of the enclosure.

12. A vacuum console as in claim 8, including a light bar display on a top of the enclosure for indicating vacuum pressure, wherein the light bar display is circular and segmented into quadrants.

* * * * *